(12) United States Patent
Albiez et al.

(10) Patent No.: US 8,481,933 B2
(45) Date of Patent: Jul. 9, 2013

(54) METHOD AND DEVICE FOR EXAMINING A SURFACE OF AN OBJECT

(75) Inventors: Michael Albiez, Aalen (DE); Wolfram Buhler, Hermaringen (DE)

(73) Assignee: Carl Zeiss Microscopy GmbH, Jena (DE)

( * ) Notice: Subject to any disclaimer, the term of this patent is extended or adjusted under 35 U.S.C. 154(b) by 573 days.

(21) Appl. No.: 12/460,166

(22) Filed: Jul. 14, 2009

(65) Prior Publication Data
US 2010/0102223 A1 Apr. 29, 2010

Related U.S. Application Data

(60) Provisional application No. 61/134,960, filed on Jul. 15, 2008.

(30) Foreign Application Priority Data

Jul. 15, 2008 (DE) .......................... 10 2008 040 426

(51) Int. Cl.
*H01J 37/26* (2006.01)
(52) U.S. Cl.
USPC ........... 250/310; 250/306; 250/307; 250/309; 430/296
(58) Field of Classification Search
USPC .......... 250/306, 307, 309, 310, 311; 430/296, 430/298
See application file for complete search history.

(56) References Cited

U.S. PATENT DOCUMENTS

| | | | |
|---|---|---|---|
| 4,660,297 A | 4/1987 | Danielson | |
| 5,396,067 A | 3/1995 | Suzuki et al. | |
| 6,105,589 A | 8/2000 | Vane | |
| 6,525,317 B1 | 2/2003 | Yang | |
| 6,555,815 B2 | 4/2003 | Feuerbaum et al. | |
| 6,753,538 B2 | 6/2004 | Musil et al. | |
| 2002/0079464 A1* | 6/2002 | Driessen et al. | 250/492.1 |
| 2002/0136674 A1 | 9/2002 | Vane | |
| 2004/0262515 A1 | 12/2004 | Motoi et al. | |
| 2005/0279934 A1* | 12/2005 | Stewart et al. | 250/310 |
| 2007/0194228 A1 | 8/2007 | Frosien et al. | |
| 2008/0302954 A1* | 12/2008 | Phaneuf et al. | 250/251 |
| 2009/0260112 A1* | 10/2009 | Winkler et al. | 850/16 |
| 2011/0068265 A1 | 3/2011 | Arai et al. | |
| 2011/0279799 A1 | 11/2011 | Singer et al. | |

FOREIGN PATENT DOCUMENTS

| | | |
|---|---|---|
| DE | 33 32 248 A1 | 3/1985 |
| DE | 102 08 043 A1 | 9/2003 |
| DE | 103 01 579 A1 | 7/2004 |

(Continued)

OTHER PUBLICATIONS

Winkler, Dieter et al., "E-beam probe station with integrated tool for electron beam induced etching", *Microelectronic Engineering* 31 (1996), pp. 141-147.

(Continued)

*Primary Examiner* — Nicole Ippolito
(74) *Attorney, Agent, or Firm* — Muirhead and Saturnelli, LLC

(57) ABSTRACT

A method for treating a surface of an object and a device suitable in particular for performing this method provide for examining the surface of the object with the aid of a particle beam to counteract the charge buildup on the object. A gas is supplied to convey the charge away from the surface and/or to neutralize it.

72 Claims, 15 Drawing Sheets

FOREIGN PATENT DOCUMENTS

| | | | |
|---|---|---|---|
| DE | 10 2007 051459 A1 | 5/2009 | |
| EP | 0 969 494 A1 | 1/2000 | |
| EP | 1 577 927 A2 | 9/2005 | |
| WO | WO03071578 A2 | 8/2003 | |
| WO | WO2004/064097 A2 | 7/2004 | |
| WO | WO 2009/053476 A1 | 4/2009 | |

OTHER PUBLICATIONS

Press Release "Zeiss Ultra plus—Breakthrough in Ultra-High-Resolution Imaging of Non-Conductive Samples," Carl Zeiss SMT AG, Aug. 2007, 3 pp.

ULTRA plus Product Chart, "New: ULTRAplus—Analytical ultra high-end FE-SEM for Nano-Research," Zeiss, 1 p, 2007.

ULTRA plus Brochure, "The New Significant Combination 2 See More," Carl Zeiss SMT, Ver. 11-07, 8 pp, 2007.

Zeiss CrossBeam Series Brochure, "Cutting Edge Technology Delivering Unique Solutions," Carl Zeiss SMT, Ver. 08-07, 32 pp, 2007.

Casey Jr., J. David et al., "Gas-Assisted Etching with Focused Ion Beam Technology," *Microelectronic Engineering* 24 (1994), pp. 43-50.

Moncrieff D A et al., "Charge neutralization of insulating surfaces in the SEM by gas ionization," *Applied Physics* 11 (1978), pp. 2315-2325.

Robinson, V N E, "The elimination of charging artefacts in the scanning electron microscope," *Journal of Physics E: Scientific Instruments* 8 (1975), pp. 638-640.

\* cited by examiner

METHOD AND DEVICE FOR EXAMINING A SURFACE OF AN OBJECT

RELATED APPLICATIONS

This application claims priority to U.S. Provisional App. No. 61/134,960, filed Jul. 15, 2008, which is incorporated herein by reference.

TECHNICAL FIELD

This application relates to a method for examining a surface of an object and a device suitable for performing this method.

BACKGROUND OF THE INVENTION

Electron beam devices, in particular scanning electron microscopes, are used for examining surfaces of objects. To do so, with a scanning electron microscope, an electron beam (hereinafter also referred to as a primary electron beam) is generated by a beam generator and focused by a beam guidance system on the object to be examined. The primary electron beam is guided by a deflecting device in a grid pattern over the surface of the object to be examined. The electrons of the primary electron beam then interact with the object. As a result of this interaction, in particular, electrons are emitted from the object surface (so-called secondary electrons) or electrons of the primary electron beam are backscattered (so-called backscattered electrons). The secondary electrons and backscattered electrons are detected and used to generate an image. This thus yields an image of the surface of the object to be examined. Reference is made here to DE 103 01 579 A1 as an example, which is incorporated herein by reference.

It is also known from the related art that an electron beam device may be used for treating the surface of an object. More specifically, it is known that the surface of an object may be etched, the etching being induced by an electron beam. With the known method, a gas is guided to the surface of the object and is adsorbed by the surface of the object. A reaction of the gas with the surface of the object is induced by the electron beam which is rasterized over the surface of the object, forming a volatile reaction product which is removed by pumping. As an example, reference is made here to the publication "E-beam probe station with integrated tool for electron beam induced etching" (Elektronenstrahlsonden-Station mit integriertem Gerät zum mittels Elektronenstrahl induzierten Ätzen) (Dieter Winkler, Hans Zimmermann, Margot Mangerich, Robert Trauner, *Microelectronic Engineering* 31 (1996), 141-147), which is incorporated herein by reference.

Furthermore, it is also known from the related art that a scanning electron microscope may be equipped with an ion beam column. Ions which are used for preparation of objects (e.g., polishing an object or applying material to the object) or for imaging are generated by an ion beam generator situated in the ion beam column. For example, it is possible in this way to obtain three-dimensional information about an object to be examined. Therefore, image series are recorded by a scanning electron microscope. Between two images of the image series, the object to be examined is prepared. Three-dimensional models of the object to be examined may be calculated by combining the images of the image series.

All the devices described here have a disadvantage. If a nonconductive object is to be examined or treated by an electron beam, the object develops a charge. This influences in particular the electron beam directed at the object. The imaging of the surface of the object is also influenced. In the worst case, features of the surface of the object are no longer imaged properly.

To avoid this effect, a scanning electron microscope, which is used for imaging objects and is provided with a gas feed mechanism guiding an inert gas to the surface of the object, is known from the related art. The inert gas forms a layer covering the area where a primary electron beam strikes the object. This should prevent or reduce charging of an object.

Furthermore, a system is known from the related art for dissipating charges from samples in scanning electron microscopic examinations. With this system, a gas stream is directed in a targeted manner at an area of an object to be imaged. The gas molecules dissociate there into positive ions and low-energy electrons due to the interaction with the primary electron beam and secondary electron beam. The positive ions are accelerated toward the negatively charged surface of the object to be imaged, where they pick up electrons from the surface in a neutralization process and are then drawn back away from the surface of the object as a neutral gas.

With regard to the discharge methods described here, reference is made to U.S. Pat. No. 6,555,815 B2 and DE 33 32 248 A1 as examples, which are incorporated herein by reference.

Accordingly, it would be desirable to provide a method for examining a surface with the aid of a particle beam, which counteracts the charge buildup on an object to be treated in a particularly effective manner. Furthermore, it would be desirable to provide a particle beam device which is suitable for performing the method.

SUMMARY OF THE INVENTION

According to the system described herein, a method is provided of examining a surface of an object with the aid of a particle beam in which the object is situated in a sample chamber. The method according to the system described herein has the following steps: supplying the particle beam to a preselectable location on the surface of the object and supplying at least one gas to the preselectable location, such that the gas provides a charge neutralization and/or a charge distribution away from the preselectable location (both individually or together, also referred to below as charge compensation) and/or for removal or avoidance of contamination of the object and has a partial pressure greater than or equal to 20 Pa, with a total pressure less than or equal to 1 Pa prevailing in the sample chamber during the gas feed. For example, the total pressure in the sample chamber is less than or equal to 0.5 Pa or less than or equal to 0.1 Pa, for example. The partial pressure of the gas is the local partial pressure at the preselectable location or in the immediate vicinity of the preselectable location. The total pressure, however, is the pressure averaged over a larger portion of the volume of the sample chamber. For example, this pressure is measured far away from the object on the wall of the sample chamber.

The system described herein is based on the idea that a charge which occurs at a preselectable location due to an interaction of a particle beam with the surface of an object and which is situated at the location of the surface of the object to be treated and/or imaged, if necessary (i.e., the preselectable location) is in particular readily removable by charge compensation (i.e., charge neutralization and/or a distribution of the charge away from the preselectable location) under the stated parameters with regard to the partial pressure of the gas and the total pressure in the sample chamber.

In charge neutralization, the gas at the preselectable location forms a local cloud of gas over the preselectable location. Interaction particles, e.g., secondary electrons and backscattered electrons which are formed due to the interaction of the particle beam with the object, ionize gas molecules of this cloud of gas. The resulting ions, e.g., positive ions, then strike the object and neutralize the surface of the object with regard to the resulting charge. Alternatively and/or additionally, the charge is guided away from the preselectable location and along the surface of the object by the ionized gas molecules, so that less charge remains at the preselectable location itself.

The system described herein has the advantage that high-voltage power supplies for a particle beam device using which the aforementioned method is performed as well as high-voltage power supplies for detectors positioned in or on the particle beam device may remain activated at all times. This allows rapid switching between an imaging mode and a charge compensation mode, so that the three-dimensional models of the object to be examined already described above may be calculated more rapidly because of the faster recording of images.

In an embodiment of the method according to the system described herein, the gas is supplied as a first gas to the preselectable location on the surface of the object. In addition, a second gas is also supplied to the preselectable location on the surface of the object. The second gas is not provided for charge compensation but instead is provided for treating the surface of the object at the preselectable location. More specifically, the second gas is used in treating the surface of the object at the preselectable location for a process induced by the particle beam.

In another embodiment of the method according to the system described herein, the supply of the first gas and the supply of the second gas take place simultaneously. This embodiment thus ensures that simultaneous treatment of the preselectable location and charge compensation are possible. As an alternative to this, it is provided that the first gas is supplied only after the supply of the second gas is concluded. Thus, in this embodiment, the preselectable location is treated first and only then does charge compensation take place.

In another embodiment of the method according to the system described herein, the first gas has a first partial pressure while the second gas has a second partial pressure. The first partial pressure is the local partial pressure of the first gas at the preselectable location or in its immediate vicinity. The second partial pressure is the local partial pressure of the second gas at the preselectable location or in its immediate vicinity. In this embodiment, the first partial pressure and the second partial pressure are now selected in such a way that the first partial pressure is higher than the second partial pressure, e.g., much higher than the second partial pressure. The first partial pressure of the first gas used for the charge compensation is thus higher than the second partial pressure of the second gas used for the treatment of the preselectable location on the surface of the object.

In an embodiment, the first partial pressure may be selected in such a way that it is in the range from 20 Pa to 100 Pa, e.g., in the range from 30 Pa to 80 Pa. In another embodiment, the first partial pressure is in the range of 40 Pa to 60 Pa. In another embodiment, the second partial pressure of the second gas may be selected so that it is in the range from 0.01 Pa to 0.5 Pa, e.g., in the range from 0.05 Pa to 0.3 Pa.

In another embodiment, it is provided that in the method according to the system described herein, an inert gas is used as the first gas and a process gas is supplied as the second gas. For example, $XeF_2$ and $Cl_2$ are suitable as the process gas. However, the system described herein is not limited to these process gases. Instead, any process gas which is suitable for treating a surface of an object may be used. For example, nitrogen or argon may be used as the inert gas. However, the system described herein is not limited to these inert gases. Instead, any inert gas may be used if it is suitable for charge compensation. Furthermore, it is pointed out that the first gas and the second gas need not be different gases. Instead, the same gas may also be used as the first gas and the second gas.

In another embodiment of the method according to the system described herein, multiple particle beams may be used. Thus, in this embodiment, the aforementioned particle beam is embodied as a first particle beam for imaging the surface of the object. In addition, in this embodiment, a second particle beam is provided which is used for treating the surface of the object. For example, the first particle beam is embodied as an electron beam while the second particle beam is embodied as an ion beam.

In another embodiment, the method according to the system described herein may provide for examination of a surface of an object that may be contaminated with carbon in such a way that proper imaging of the surface of the object is very difficult. Accordingly, in this embodiment, a reactive gas or a mixture of a reactive gas with an inert gas may be guided to the preselectable location on the surface of the object. In this way, the carbon is removable from the surface of the object, in particular from the preselectable location on the surface of the object. For example, room air or a mixture of nitrogen and oxygen is suitable as the reactive gas.

In another embodiment of the method according to the system described herein, a high voltage potential may be applied between the object and a detector, so that particles emerging from the object (e.g., electrons) and/or particles scattered on the object (e.g., electrons) are accelerated in the direction of the detector, so that the high voltage potential remains activated during the supply of gas which is used for charge compensation.

According to yet another embodiment of the method according to the system described herein, a high voltage potential may be applied between the object and an electrode of an electrostatic lens or between two electrodes of an electrostatic lens, the high voltage potential remaining activated during the supply of gas which is used for charge compensation.

According further to the system described herein, a particle beam device is provided that is suitable for performing a method having at least one of the aforementioned features or feature combinations. The particle beam device according to the system described herein may have at least one particle beam column, which is provided with at least one beam generator for generating a particle beam and at least one beam guidance system for guiding the particle beam. Furthermore, the particle beam device according to the system described herein may be provided with a sample chamber. At least one object having a surface on which there is a preselectable location to which the particle beam is guidable by the beam guidance system is provided in the sample chamber. In addition, the particle beam device according to the system described herein has at least one gas supply unit for supplying a gas to the preselectable location, the gas being used for a charge neutralization and/or a charge distribution away from the preselectable location (also referred to below as charge compensation both individually or together) and/or for removal or avoidance of contamination of the object as well as having a partial pressure greater than or equal to 20 Pa, with a total pressure of less than or equal to 1 Pa prevailing in the sample chamber during the supply of the gas. The partial pressure of the gas is the local partial pressure at the preselectable location or in the immediate vicinity of the preselectable location. In contrast, the total pressure is the pressure averaged over a larger portion of the volume of the sample chamber. For example, it is measured at a greater distance from the object on a wall of the sample chamber.

The particle beam device according to the system described herein may be based on the same considerations as the method according to the system described herein. Therefore, reference is made to the comments made above.

In an embodiment of the system described herein, the total pressure in the sample chamber during the supply of the gas may be less than or equal to 0.5 Pa or less than or equal to 0.1 Pa, for example.

In another embodiment of the particle beam device according to the system described herein, several particle beam columns may be provided. Thus, the particle beam column mentioned above may be embodied as a first particle beam column, the beam generator being provided as a first beam generator for generating the first particle beam, and the beam guidance system being provided as a first beam guidance system. Furthermore, a second particle beam column may be provided, having a second beam generator for generating a second particle beam and a second beam guidance system guiding the second particle beam to the preselectable location. For example, imaging of the preselectable location is performed by the first particle beam, while the second particle beam is provided for treating the preselectable location. Specific embodiments of the system described herein in which the treatment of the preselectable location is performed by the first particle beam while the second particle beam is provided for imaging the preselectable location are of course also provided.

In another embodiment of the particle beam device according to the system described herein, the gas supply unit may be embodied as a first gas supply unit for supplying a first gas to the preselectable location on the surface of the object. In addition, at least one second gas supply unit is provided for supplying a second gas to the preselectable location on the surface of the object. The second gas is used for treating the surface of the object at the preselectable location as already explained above.

The particle beam device according to the system described herein is not limited to use of only two gas supply units, namely the first gas supply unit and the second gas supply unit. Instead, exemplary embodiments of the particle beam device according to the system described herein are provided in which more than two supply units are assigned to the particle beam device. In these embodiments, one of the more than two gas supply units supplies the first gas, so that charge is compensated, e.g., neutralized, at the preselectable location. The other gas supply units of the more than two gas supply units supply process gases, for example.

In another embodiment of the particle beam device according to the system described herein, the first gas supply unit and the second gas supply unit may operate independently of one another. In this embodiment, the two gas supply units do not depend on one another. Instead, the units are completely independent of one another and may be situated at different locations in the particle beam device according to the system described herein.

In another embodiment of the particle beam device according to the system described herein, the first gas supply unit and the second gas supply unit may be assigned to a single gas inlet system. For example, the gas inlet system forms a unit having multiple gas supply tanks, supplying the first gas to the first gas supply unit and the second gas to the second gas supply unit. In addition, in another embodiment, the first gas and the second gas may be conveyed to the preselectable location via the same supply unit, the first gas being introduced into the supply unit from a first gas storage tank and the second gas being introduced into the supply unit only after that, after cutting off the first gas inlet.

In another embodiment, the first gas supply unit and/or the second gas supply unit may be situated movably. This ensures that the first gas supply unit and/or the second gas supply unit may always be positioned in the vicinity of the preselectable location, so that the first gas and/or the second gas may be conveyed easily to the preselectable location. The first gas supply unit is situated at a distance of approximately 10 µm to 1 mm from the preselectable location, for example. The same thing is true of a specific embodiment with regard to the location of the second gas supply unit.

In another embodiment of the particle beam device according to the system described herein, the first gas supply unit and/or the second gas supply unit may have at least one cannula which is movably positioned, for example. The first gas and/or the second gas may be conveyed to the preselectable location through this cannula. In an embodiment, the cannula may have a feed opening having a diameter in the range of 10 µm to 1000 µm, e.g., in the range of 400 µm to 600 µm.

Furthermore, in yet another embodiment, in the particle beam device according to the system described herein, the first gas has a first partial pressure and the second gas has a second partial pressure. The first partial pressure is the local partial pressure of the first gas at the preselectable location or in its immediate vicinity. The second partial pressure is the local partial pressure of the second gas at the preselectable location or in its immediate vicinity. The first partial pressure is higher than the second partial pressure, e.g., much higher than the second partial pressure. In an embodiment, the second partial pressure is in the range of 0.01 Pa to 0.5 Pa. In yet another embodiment, it is in the range of 0.05 Pa to 0.3 Pa. However, the first partial pressure may be in the range of 20 Pa to 100 Pa, and in other embodiments it is in the range of 30 Pa to 80 Pa or in the range of 40 Pa to 60 Pa.

In another embodiment of the particle beam device according to the system described herein, the first gas is embodied as an inert gas and the second gas is embodied as a process gas. As already explained above, $XeF_2$ and $Cl_2$ are suitable as the process gas, for example. However, the system described herein is not limited to these process gases. Instead, any process gas which is suitable for treating a surface of an object may be used. For example, nitrogen or argon is used as the inert gas. However, the system described herein is not limited to these inert gases. Instead, any inert gas suitable for charge compensation may be used. In embodiments having more than two gas supply units, one of the gas supply units may be provided for supplying an inert gas while the additional gas supply units of the more than two gas supply units supply process gases.

In another embodiment, the particle beam column may be embodied as an electron beam column or an ion beam column when using a single particle beam column. As an alternative to this, when using multiple particle beam columns, the first particle beam column may be embodied as an electron beam column, and the second particle beam column may be embodied as an ion beam column. For example, the second particle beam column creates a focused ion beam (FIB), while the first particle beam column is embodied as a scanning electron column. Such a combination of an ion beam column with an electron beam column allows four possible modes of operation, namely imaging by electrons, imaging by ions, treatment of the surface of the object by ions with simultaneous observation of the treatment by imaging by electrons, and treatment of the surface of the object by electrons. In all four modes of operation, charge compensation may take place at the preselectable location on the surface of the object. In another embodiment, first the preselectable location is to be treated by the ion beam and a suitable process gas, and only after the ion beam has been removed from the preselectable location and the electron beam has been introduced for imaging of the surface of the object is an inert gas to be supplied to the preselectable location to compensate a large portion of the charge from the preselectable location. As an alternative to this, first the inert gas and then the electron beam are introduced.

In another embodiment of the particle beam device according to the system described herein, a gas supply unit supplies a reactive gas and/or a mixture of a reactive gas and an inert gas to the preselectable location on the surface of the object. Carbon may be removed from the surface of the object by the reactive gas or the mixture of a reactive gas and an inert gas, as explained above.

In another embodiment, the particle beam device may be additionally provided with at least one detector, at least one high-voltage supply unit for applying a high voltage between the detector and the object and at least one control unit, which controls the supply of gas used for charge compensation and controls the high-voltage power supply unit. The control unit may operate such that in at least one operating mode the high voltage remains activated when the gas used for charge compensation is supplied.

In yet another embodiment, the particle beam device may be additionally provided with two electrodes of an electrostatic lens, at least one high-voltage power supply unit for applying a high voltage between the two electrodes of the electrostatic lens and at least one control unit which controls the supply of gas used for charge compensation and controls the high-voltage power supply unit. The control unit may operate such that in at least one operating mode the high voltage remains activated when the gas used for charge compensation is supplied.

According further to the system described herein, a method is provided for imaging and/or treating a surface of an object by at least one process induced by a particle beam, the process having the following steps: supplying at least one first gas to at least one preselectable location on the surface of the object, supplying the particle beam to the preselectable location, the particle beam interacting with the first gas in such a way that the surface of the object is treated at the preselectable location, supplying at least one second gas to the preselectable location and neutralizing a charge at the preselectable location on the surface of the object. In addition, the method described above may have one or more of the method features defined above.

According further to the system described herein, a particle beam device has at least one particle beam column that includes at least one beam generator for generating a particle beam and at least one beam guidance system for guiding the particle beam. Furthermore, the particle beam device is provided with at least one object having a surface on which there is a preselectable location to which the particle beam is guidable by the beam guidance system. At least one first gas supply unit for supplying a first gas is provided, the first gas being such that the charge at the preselectable location is neutralized. Furthermore, at least one second gas supply unit is provided for supplying a second gas, the second gas being such that the preselectable location is treatable. In addition, the particle beam device described above may have one or more of the aforementioned features.

BRIEF DESCRIPTION OF THE DRAWINGS

Embodiments of the system described herein will now be explained in greater detail based on the figures of the drawings that are briefly described as follows.

DETAILED DESCRIPTION OF VARIOUS EMBODIMENTS

Figure 1:
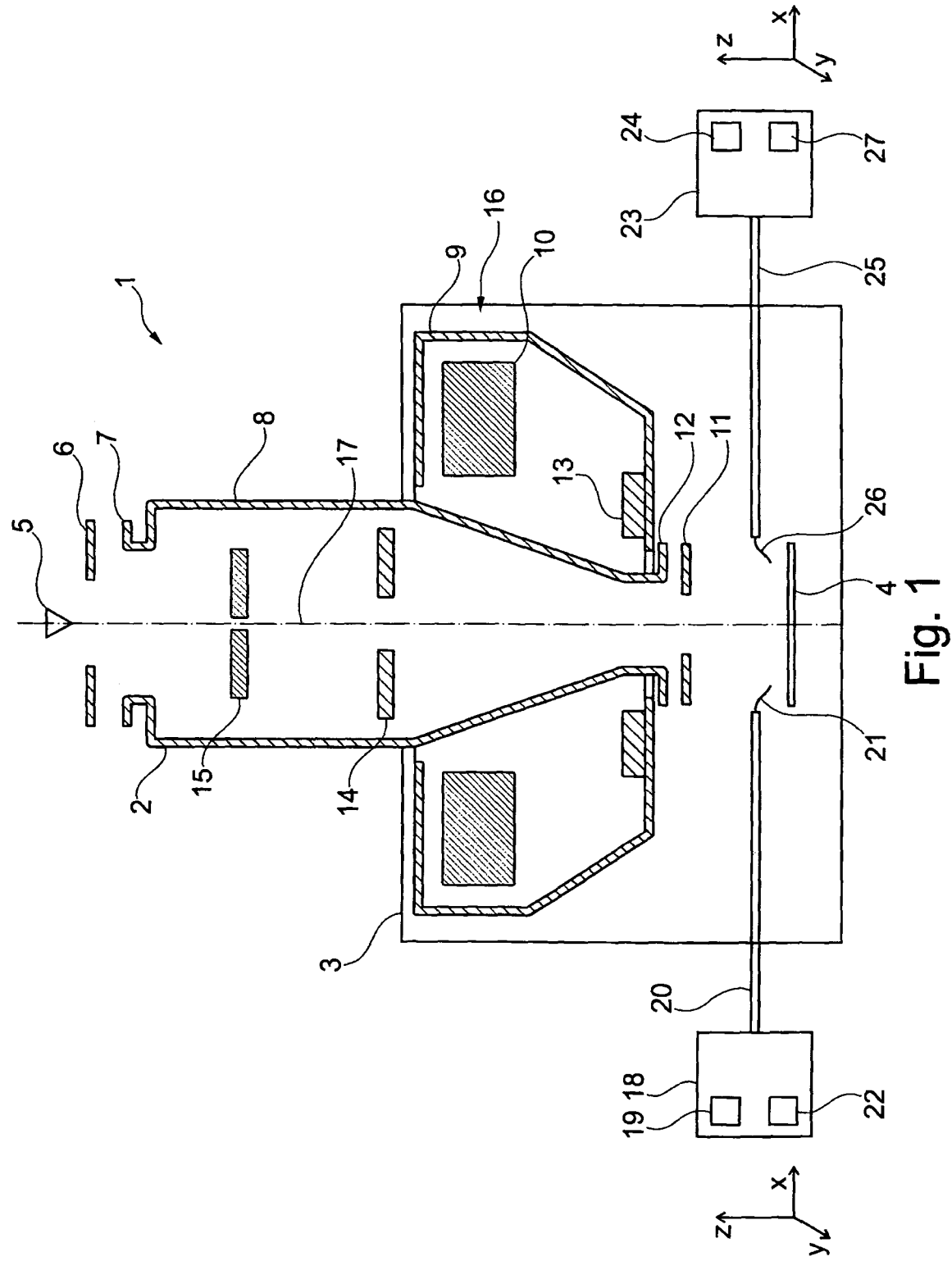
FIG. 1 shows a schematic view of a particle beam device having a single particle beam column and two movably positioned gas supply units.

FIG. 1 shows a schematic view of a particle beam device 1 equipped with a single particle beam column 2 according to an embodiment of the system described herein. Particle beam column 2 is an electron beam column or an ion beam column, for example. It is assumed below that this illustrated embodiment is provided with an electron beam column.

Furthermore, particle beam device 1 is equipped with a sample chamber 3, in which an object 4 that is to be examined and/or treated is situated. Particle beam device 1 is used on the one hand for imaging a certain preselectable region (preselectable location) on the surface of object 4 and on the other hand for treating this preselectable location (e.g., by removal of material or by addition of material).

Particle beam device 1 has a beam generator 5 in the form of an electron source (cathode) and a system which includes a first electrode 6 and a second electrode 7. Second electrode 7 forms one end of a beam guidance tube 8. For example, beam generator 5 is embodied as a thermal field emitter. Electrons emerging from beam generator 5 are accelerated to a preselectable potential due to a potential difference between beam generator 5 and second electrode 7 and form a primary electron beam. Beam guidance tube 8 is guided through an opening of a magnetic lens, acting as an objective lens 16. Objective lens 16 is equipped with pole shoes 9, which contain coils 10. An electrostatic delay unit is connected downstream from beam guidance tube 8. It has a single electrode 11 and a tube electrode 12 situated at the end of beam guidance tube 8, which is opposite object 4. Tube electrode 12 together with beam guidance tube 8 is thus at anode potential, while single electrode 11 and object 4 are at a lower potential than anode potential. Electrons of the primary electron beam may then be decelerated in this way to a desired energy, which is required for the examination and/or treatment of object 4. Beam guidance tube 8 is, for example, 5 kV to 30 kV positive, in particular 8 kV to 15 kV positive in comparison with object 4 and single electrode 11, so that after emerging from beam guidance tube 8 electrons are decelerated to a target energy with which they are to strike object 4. Furthermore, rasterizing unit 13 is provided by which the primary electron beam may be deflected and rasterized over object 4.

Secondary electrons and/or backscattered electrons, which are formed due to the interaction of the primary electron beam with the object, are detected by a detector system in beam guidance tube 8 for imaging. To do so, a first detector 14 is situated at the object end along the optical axis 17 in beam guidance tube 8, while a second detector 15 is situated along optical axis 17 at the source end (i.e., in the direction of beam generator 5). Furthermore, first detector 14 and second detector 15 are offset from one another.

Particle beam device 1 also has a first gas supply unit 18, which is used to supply a first gas in the form of an inert gas to a preselectable location on the surface of object 4. The first gas is accommodated here in a first gas tank system 19. First gas supply unit 18 is provided with a first inlet line 20 which protrudes into sample chamber 3. First inlet line 20 has a first cannula 21 in the direction of object 4; this cannula may be brought into the vicinity of the preselectable location on the surface of object 4, e.g., at a distance of 10 µm to 1 mm. First cannula 21 has a feed opening having a diameter in the range of 10 µm to 1000 µm, e.g., in the range of 400 µm to 600 µm. First gas supply unit 18 is also provided with a first adjusting unit 22, which allows adjustment of the position of first cannula 21 in all three spatial directions (x direction, y direction, z direction).

First gas supply unit 18 is diametrically opposite a second gas supply unit 23, which is provided for supplying a second gas in the form of a process gas to the preselectable location on the surface of object 4. Second gas supply unit 23 is independent of first gas supply unit 18 and thus does not have any connection to first gas supply unit 18.

The second gas is held in a second gas tank system 24. Furthermore, second gas supply unit 23 is provided with a second inlet line 25 protruding into sample chamber 3. Second inlet line 25 has a second cannula 26 in the direction of object 4; this cannula may be brought into the vicinity of the preselectable location on the surface of object 4, e.g., at a distance of 10 µm to 1 mm. Second cannula 26 has a feed opening having a diameter in the range of 10 µm to 1000 µm, e.g., in the range of 400 µm to 600 µm. Second gas supply unit 23 is also provided with a second adjusting unit 27, which allows adjustment of the position of second cannula 26 in all three spatial directions (x direction, y direction, z direction).

In other embodiments, first gas tank system 19 of first gas supply unit 18 and/or second gas tank system 24 of second gas supply unit 23 may not be situated directly on first gas supply unit 18 and second gas supply unit 23, respectively. Instead, in these additional embodiments, first gas tank system 19 and/or second gas tank system 24 may be situated on a wall of a room in which particle beam device 1 is located.

As mentioned above, second gas supply unit 23 supplies a process gas, which interacts with the primary electron beam. This makes it possible to treat the preselectable location, in the vicinity of which second cannula 26 is situated. For example, material is removed at the preselectable location.

As explained above, an unwanted charge buildup occurs on object 4 in the areas of the surface of object 4, where the primary electron beam strikes. Because of this, the disadvantages already mentioned above occur. The unwanted charge at the preselectable location is removed by charge compensation (neutralization or charge distribution) by supplying the inert gas at the preselectable location, which is to be treated and/or examined. At the preselectable location, the inert gas then forms a local cloud of gas above the preselectable location. Interaction particles, e.g., secondary electrons and backscattered electrons formed due to the interaction of the particle beam with the object, ionize the gas molecules in this cloud of gas. The resulting ions, e.g., positive ions, strike object 4 and neutralize the surface of object 4 with regard to the resulting charge. The partial pressure of the inert gas is greater than or equal to 20 Pa. The total pressure in the sample chamber remains less than or equal to 1 Pa even during the supply of the first gas and/or the second gas. The partial pressure of the inert gas is the local partial pressure at the preselectable location or in the immediate vicinity of the preselectable location. However, the total pressure is the pressure averaged over a larger portion of the volume of sample chamber 3. For example, this pressure is measured at a great distance from object 4 on a wall of sample chamber 3.

Alternatively and/or in addition to the approach described above, a charge is guided by ionized gas molecules from the preselectable location along the surface of object 4, so that less charge remains at the preselectable location itself.

The system described herein has the advantage that high-voltage power supplies of particle beam device 1 and high-voltage power supplies of first detector 14 and of second detector 15 may remain activated continuously. This allows rapid switching between an imaging mode and a charge compensation mode, so that, as already described above in greater detail, the three-dimensional models of object 4 to be examined may be calculated more rapidly based on more rapid recording of images, for example.

The partial pressure of the process gas may be much lower than the partial pressure of the inert gas. For example, the partial pressure of the process gas may be in the range of 0.01 Pa to 0.5 Pa, in particular in the range of 0.05 Pa to 0.3 Pa. However, the partial pressure of the inert gas may be in the range of 20 Pa to 100 Pa, e.g., in the range of 30 Pa to 80 Pa or in the range of 40 Pa to 60 Pa, for example. The partial pressures of the process gas and of the inert gas are local partial pressures at the preselectable location or in the immediate vicinity of the preselectable location. However, the total pressure is the pressure averaged over a larger portion of the volume of sample chamber 3.

Figure 2:
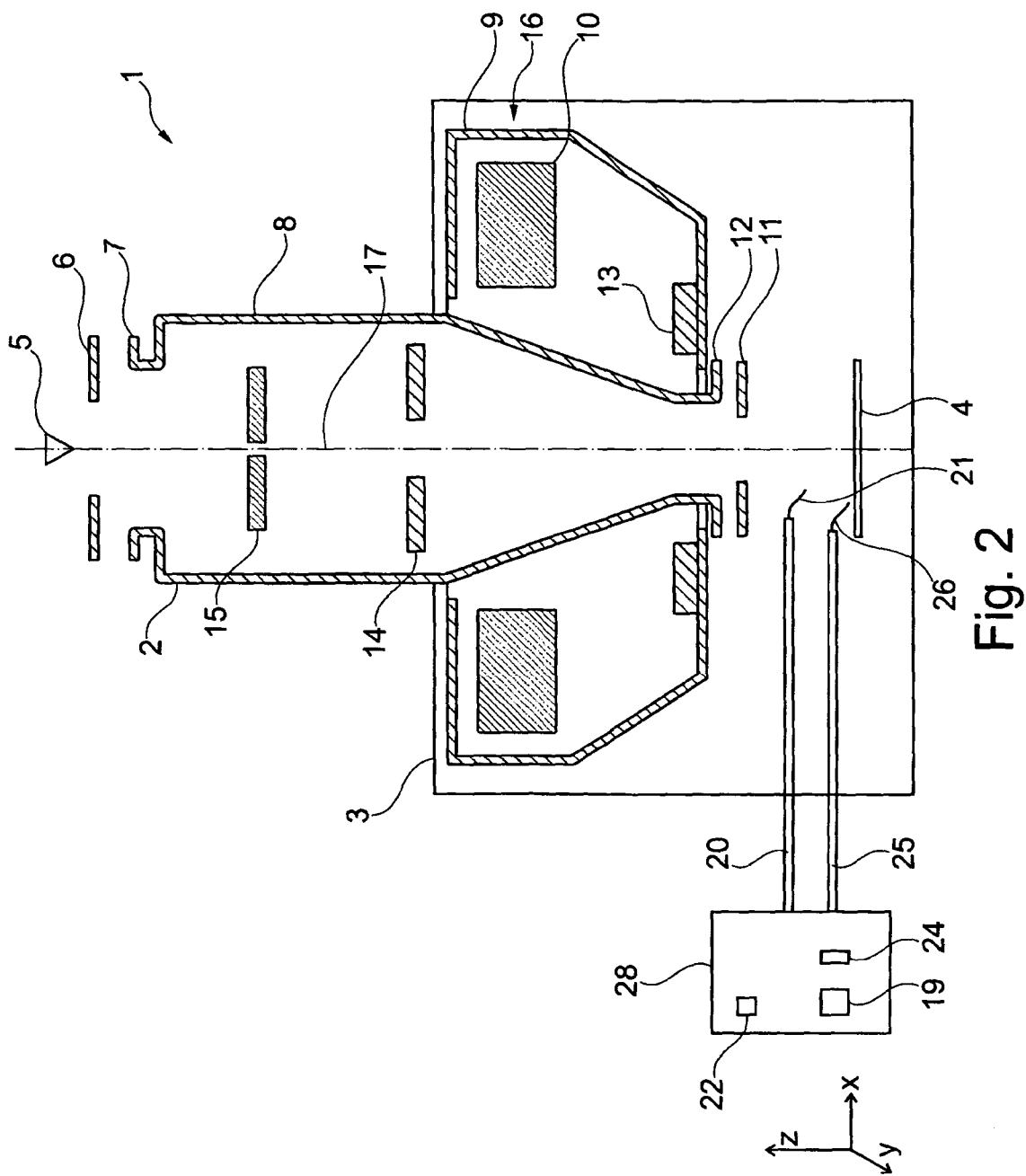
FIG. 2 shows a schematic view of another particle beam device having a single particle beam column and a gas inlet system having two movably positioned gas supply units.

FIG. 2 shows another particle beam device 1 having a single particle beam column 2 and a sample chamber 3. Particle beam device 1 of FIG. 2 may correspond to particle beam device 1 of FIG. 1. The same reference numerals therefore denote the same components. In contrast with particle beam device 1 according to FIG. 1, particle beam device 1 according to FIG. 2 has a gas inlet system 28, which is provided with a first gas tank system 19 and a second gas tank system 24. At least one inert gas is contained in first gas tank system 19 and is in turn guided to the preselectable location using a first inlet line 20 and a first cannula 21. Furthermore, at least one process gas is contained in second gas tank system 24 and is supplied to the preselectable location via a second inlet line 25 and a second cannula 26. First cannula 21 and second cannula 26 are adjustable independently of one another by an adjusting unit 22 in all three spatial directions, so that first cannula 21 and second cannula 26 may each be brought into the vicinity of the preselectable location.

Figure 3:
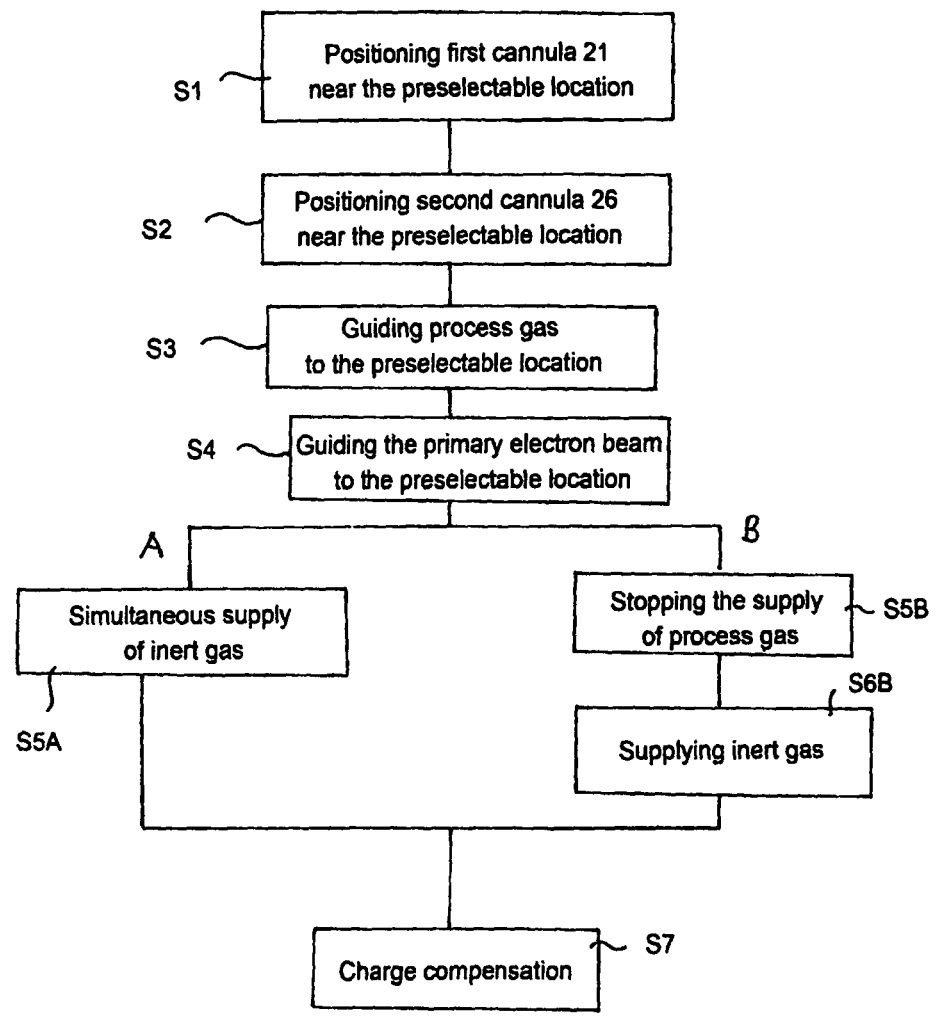
FIG. 3 shows a flow chart of a method which is used with the particle beam devices according to FIGS. 1 and 2.

FIG. 3 shows a flow chart of a method which is used with particle beam devices 1 according to FIGS. 1 and 2. In a step S1, first cannula 21 is brought into the vicinity of the preselectable location which is to be treated. In another step S2, second cannula 26 is brought into the vicinity of the preselectable location. In step S3, the process gas is guided to the preselectable location via second cannula 26. For example, the partial pressure of the process gas is in the range of 0.01 Pa to 0.5 Pa or in the range of 0.05 Pa to 0.3 Pa, for example. In step S4, the primary electron beam is brought to the preselectable location to induce a treatment procedure, e.g., removal of material, by interaction with the process gas. After this step, it is possible to select between two variants. In variant A, there is a simultaneous supply of the inert gas through first cannula 21 in step S5A. In contrast, in variant B the supply of process gas is first stopped in step S5B and only then is an inert gas supplied in a step S6B. In both variants, the partial pressure of the inert gas is in the range of 20 Pa to 100 Pa, e.g., in the range of 30 Pa to 80 Pa or in the range of 40 Pa to 60 Pa, for example. The partial pressure of the process gas is much lower than the partial pressure of the inert gas. Method step S7 which follows is again the same for both variants. In this step, charge compensation occurs as already described above. The total pressure in sample chamber 3 during the entire method is less than or equal to 1 Pa, so the advantages mentioned above are achieved. The partial pressure of the inert gas and of the process gas are local partial pressures at the preselectable location or in the immediate vicinity of the preselectable location. However, the total pressure is the pressure averaged over a large-volume of sample chamber 3.

Figure 4:
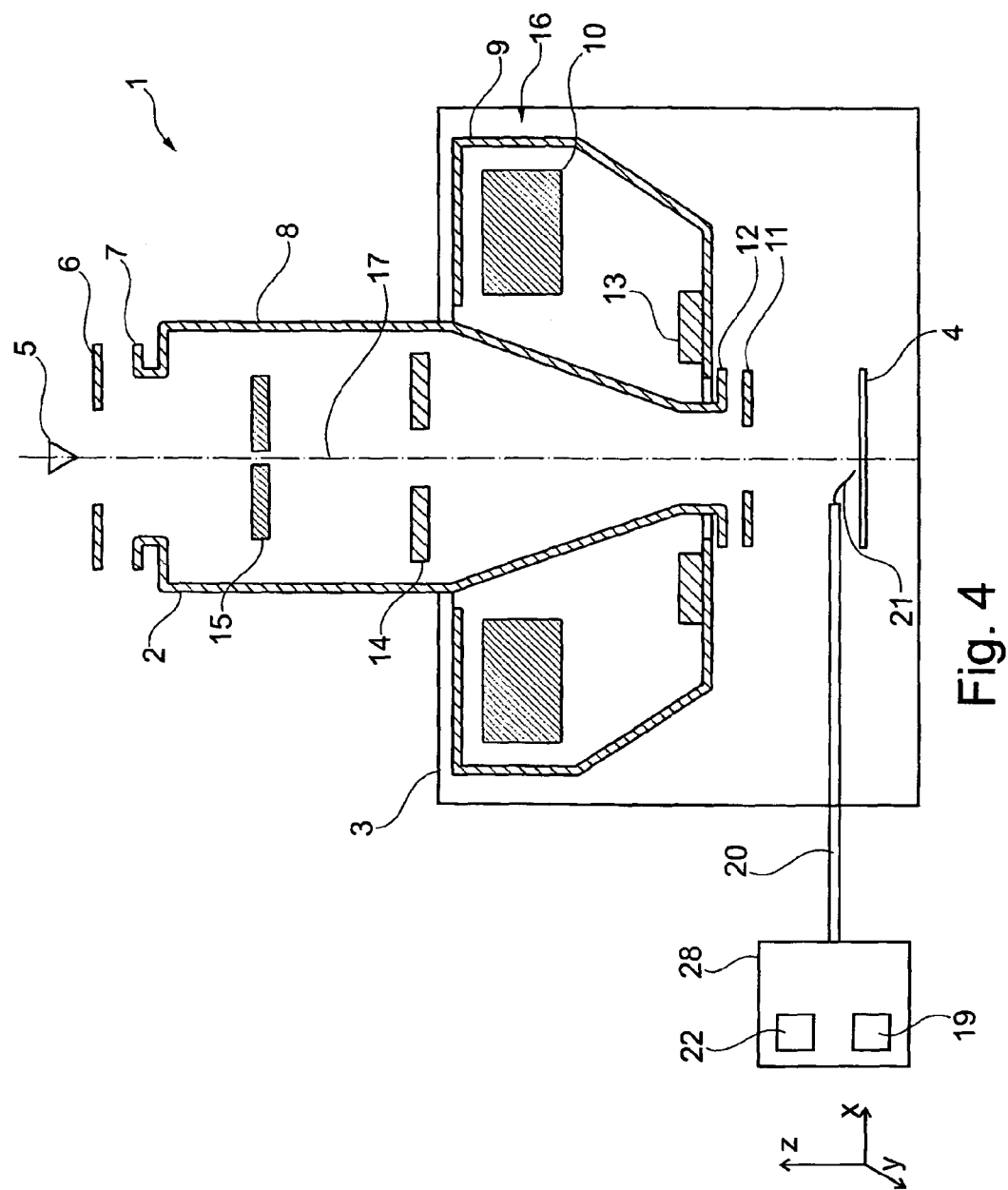
FIG. 4 shows a schematic view of another particle beam device having a single particle beam column and a single gas inlet system.
Figure 5:
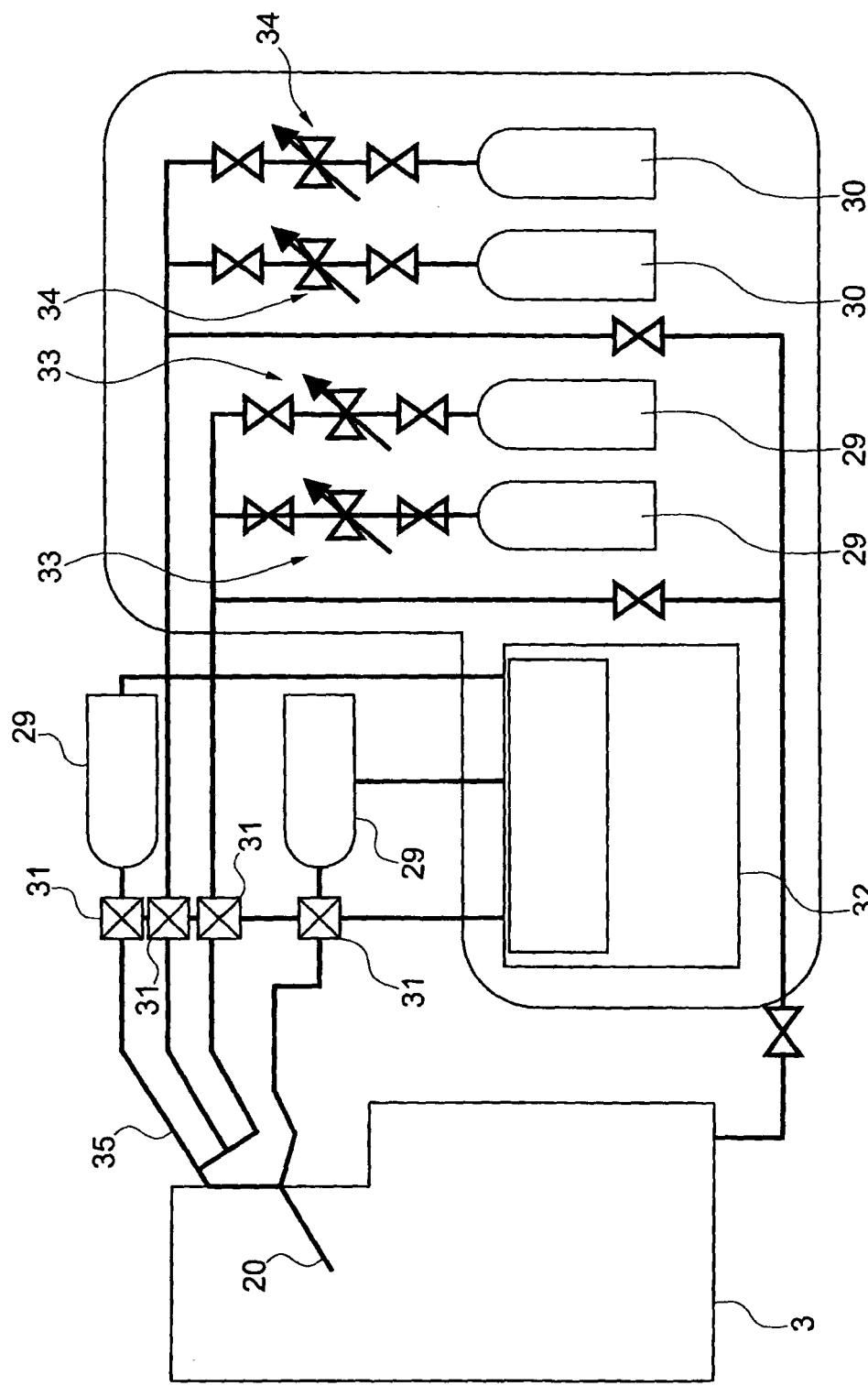
FIG. 5 shows a schematic view of the gas inlet system according to FIG. 4.

FIG. 4 shows another particle beam device 1 having an individual particle beam column 2 and a sample chamber 3. Particle beam device 1 of FIG. 4 may correspond to particle beam device 1 of FIG. 1. The same reference numerals therefore denote the same components. In contrast with particle beam device 1 according to FIG. 1, particle beam device 1 according to FIG. 4 has a gas inlet system 28, which is provided with a first gas tank system 19. First gas tank system 19 contains four process gases, which may in turn be guided individually to the preselectable location over a first inlet line 20 and a first cannula 21 by triggering a valve system. Furthermore, first gas tank system 19 has two inert gases, which may also be supplied to the preselectable location via first inlet line 20 and first cannula 21 by triggering a valve system. First cannula 21 is in turn adjustable in all three spatial directions by a first adjusting unit 22, so that first cannula 21 may be brought into the vicinity of the preselectable location. FIG. 5 shows a schematic view of gas inlet system 28. First inlet line 20, which is connected to a system of several lines 35, protrudes into sample chamber 3. Lines 35 connect first inlet line 20 to storage containers 29, where various process gases are stored for treating the preselectable location, and also to storage containers 30, which contain various inert gases. A control unit 32 opens and closes valves 31 as needed, in such a way that a process gas and/or an inert gas flow(s) through lines 35 into first inlet line 20. In addition, a first valve system 33 and a second valve system 34 are provided, regulating the flow of process gases and inert gases. In an alternative embodiment of aforementioned gas inlet system 28, an inlet line 20 is provided with a cannula situated accordingly on particular inlet line 20 for each individual process gas and for each individual inert gas.

Figure 6:
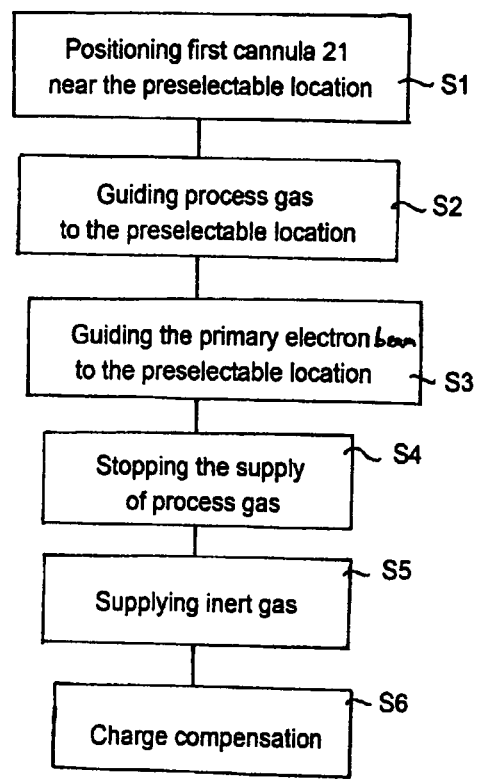
FIG. 6 shows a flow chart of a method used with the particle beam device according to FIG. 4.

FIG. 6 shows a flow chart of a method which is performed in particular in connection with particle beam device 1 according to FIG. 4. In a step S1, first cannula 21 is brought into the vicinity of the preselectable location, which is to be treated. In step S2, a process gas is supplied to the preselectable location through first cannula 21. For example, the partial pressure of the process gas is in the range of 0.01 Pa to 0.5 Pa or in the range of 0.05 Pa to 0.3 Pa, for example. In another step S3, the primary electron beam is brought to the preselectable location to induce a treatment operation, e.g., removal of material, by interaction with the process gas. In step S4, the supply of process gas is first stopped and only then in a step S5 an inert gas is supplied. The partial pressure of the inert gas is in the range of 20 Pa to 100 Pa or in the range of 30 Pa to 80 Pa, for example, or in the range of 40 Pa to 60 Pa, for example. The partial pressure of the process gas is much lower than the partial pressure of the inert gas. Charge compensation occurs in step S6 as described above. The total pressure in sample chamber 3 is less than or equal to 1 Pa during the entire process. With regard to the partial pressures of the inert gas and the process gas and with regard to the total pressure, the comments already made above are applicable.

Figure 7:
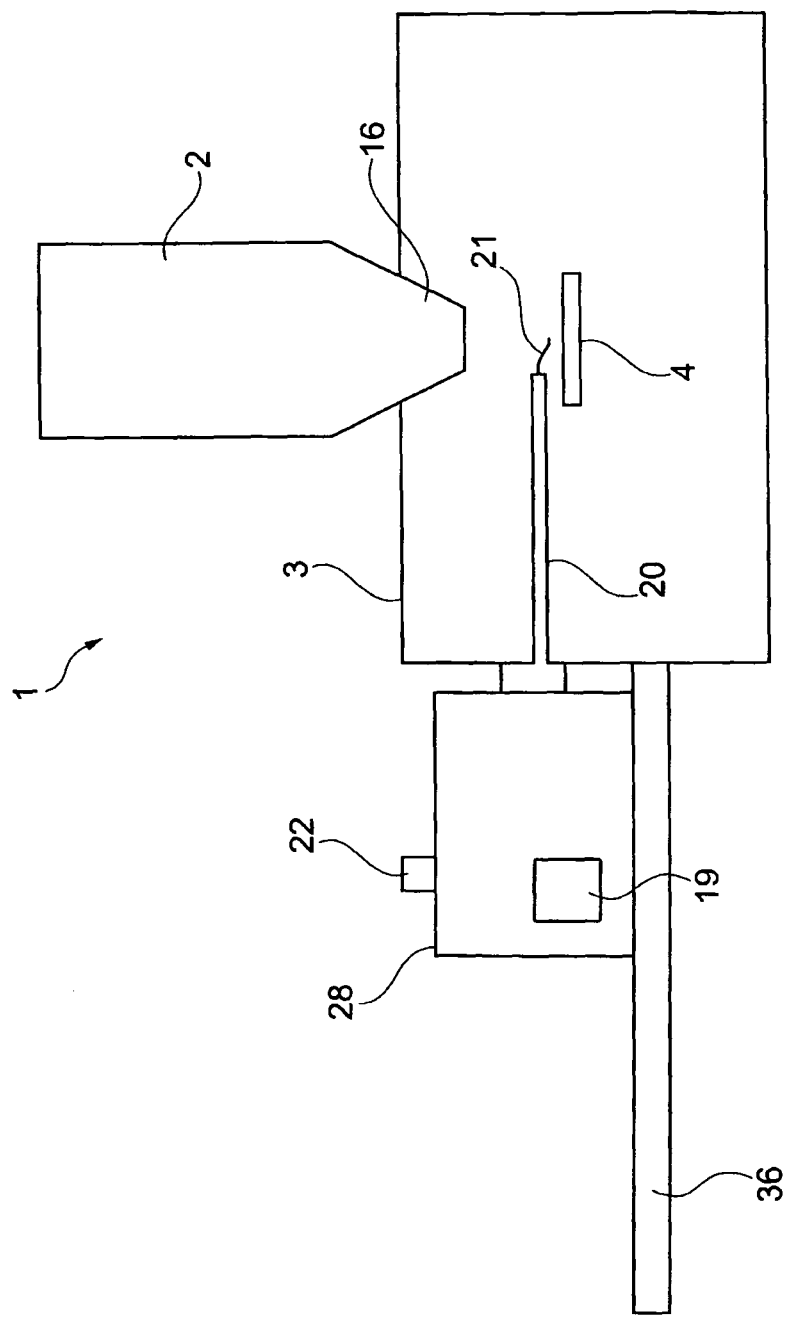
FIG. 7 shows a schematic view of another particle beam device having a single particle beam column and a gas supply unit situated beneath an objective lens.
Figure 8:
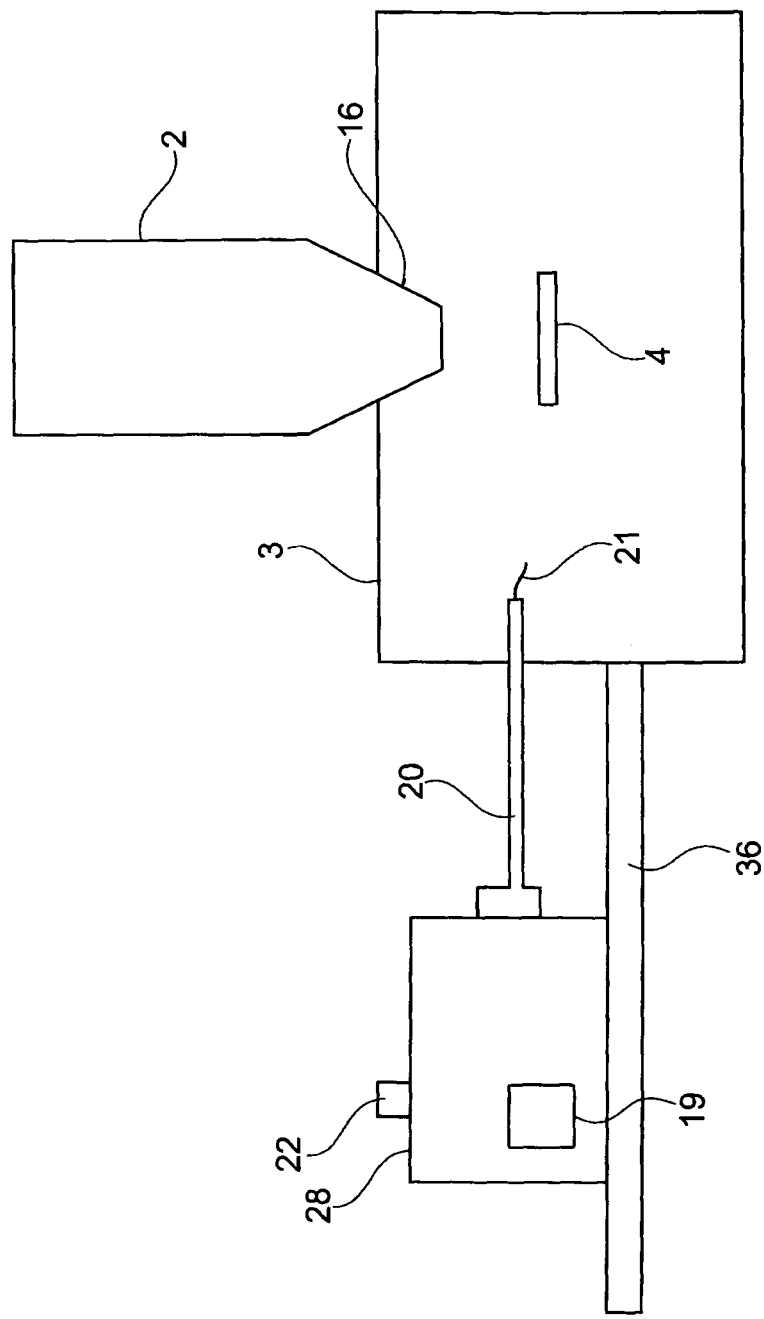
FIG. 8 shows a schematic view of the particle beam device according to FIG. 7 with the gas supply unit retracted.

FIGS. 7 and 8 show another particle beam device 1 having a single particle beam column 2 and a sample chamber 3 in a schematic view. Particle beam device 1 of FIGS. 7 and 8 may correspond to particle beam device 1 of FIG. 4. The same components are provided with the same reference numerals. It is clearly apparent here that gas inlet system 28 is situated on a carriage 36, so that first cannula 21 is brought to the vicinity of the preselectable location (see FIG. 7) or may be removed from this location (see FIG. 8). It is pointed out explicitly that the design of gas inlet system 28 shown here may also be implemented with the gas supply units already discussed and/or with the gas inlet system already discussed of the additional exemplary embodiments.

Figure 9:
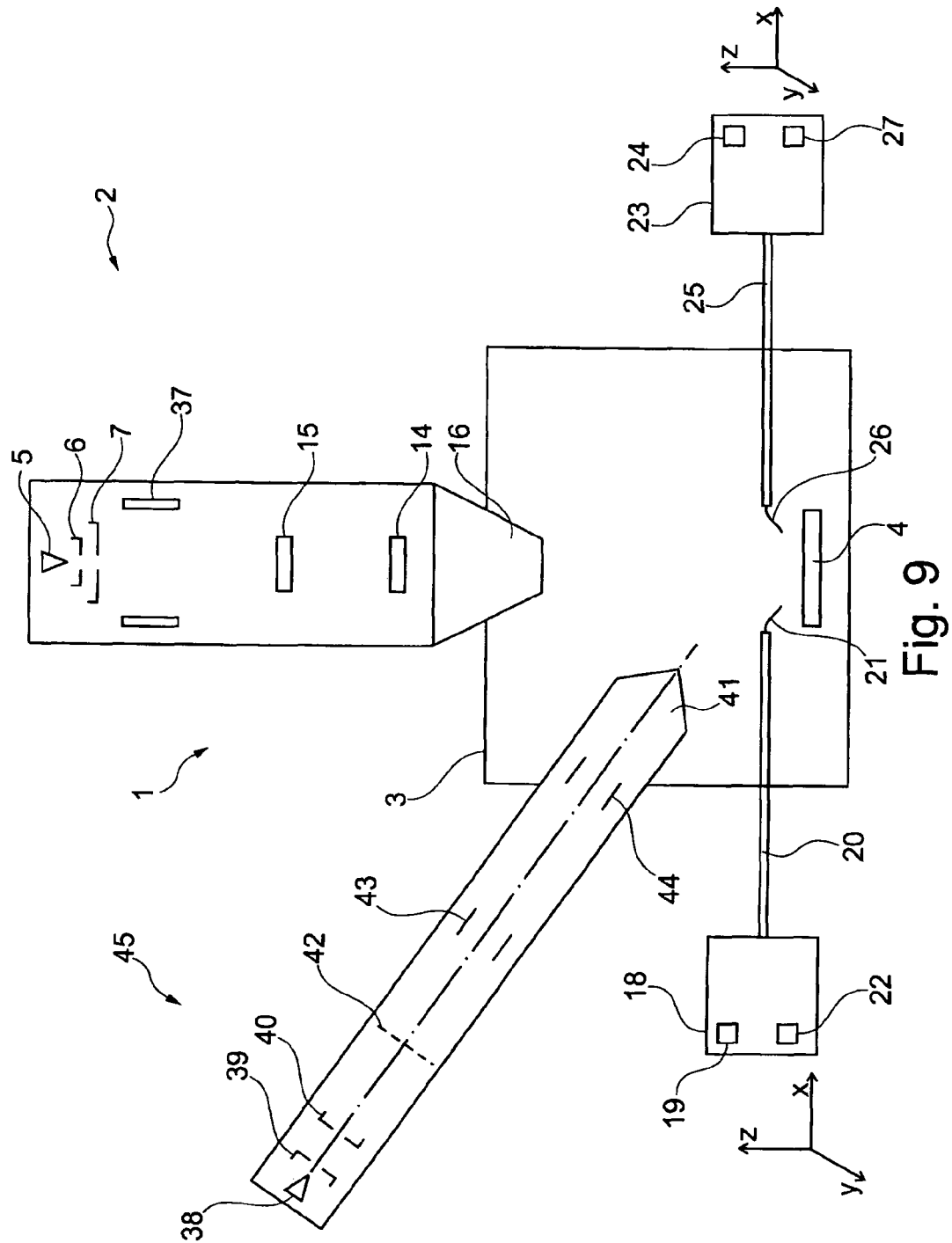
FIG. 9 shows a schematic view of a particle beam device having two particle beam columns and two movably positioned gas supply units.

FIG. 9 shows a schematic view of a particle beam device 1 having two particle beam columns, namely a first particle beam column 2 and a second particle beam column 45, which are situated on a sample chamber 3. First particle beam column 2 is embodied as an electron beam column and is situated vertically with regard to sample chamber 3. First particle beam column 2 has the same design as particle beam column 2 according to FIG. 1. The same components are thus provided with the same reference numerals. In addition, a condenser 37 for the primary electron beam is also shown.

Second particle beam column 45 is embodied as an ion beam column and is situated so that it is tilted by an angle of approximately 54° to first particle beam column 2. Second particle beam column 45 has an ion beam generator 38, which generates ions forming an ion beam. The ions are accelerated by an extraction electrode 39 to a preselectable potential. The ion beam then passes through ion optics of second particle beam column 45, where the ion optics have a condenser lens 40 and a system of additional lenses 41. Finally, lenses 41 (objective lens) generate an ion probe which strikes object 4. An adjustable aperture 42, a first electrode system 43, and a second electrode system 44 are situated above lenses 41 (i.e., in the direction of ion beam generator 38), first electrode system 43 and second electrode system 44 being embodied as scanning electrodes. The ion beam is rasterized over the surface of object 4 by first electrode system 43 and second electrode system 44.

Second particle beam column 45 has two functions. On the one hand, it images an area of interest (i.e., a preselectable location) on the surface of object 4. On the other hand, however, it also treats the area of interest (i.e., the preselectable location) on the surface of object 4. For the latter, particle beam device 1 is provided with a second gas supply unit 23. Second gas supply unit 23 supplies a second gas in the form of a process gas to the preselectable location on the surface of object 4. Second gas supply unit 23 corresponds to second gas supply unit 23 according to FIG. 1, so that reference is made to the preceding comments for additional details.

Second gas supply unit 23 is diametrically opposite a first gas supply unit 18, which is provided for supplying a first gas in the form of an inert gas, such as nitrogen or argon, to the preselectable location on the surface of object 4. First gas supply unit 18 is independent of second gas supply unit 23 and thus does not have any connection to second gas supply unit 23. First gas supply unit 18 according to FIG. 9 corresponds to first gas supply unit 18 according to FIG. 1, so that reference is made to the preceding comments for additional details.

This illustrated embodiment also ensures discharging of the preselectable location which is to be treated by the aforementioned charge compensation effect.

In this embodiment (as well as those that follow), the partial pressure of the process gas is much lower than the partial pressure of the inert gas. For example, the partial pressure of the process gas may be in the range of 0.01 Pa to 0.5 Pa or in the range of 0.05 Pa to 0.3 Pa, for example. However, the partial pressure of the inert gas may be in the range of 20 Pa to 100 Pa or in the range of 30 Pa to 80 Pa, for example, or in the range of 40 Pa to 60 Pa, for example. The total pressure in sample chamber 3 is less than or equal to 1 Pa. The preceding discussion also applies with regard to the properties of the partial pressures of the inert gas, the process gas, and the total pressure.

Figure 10:
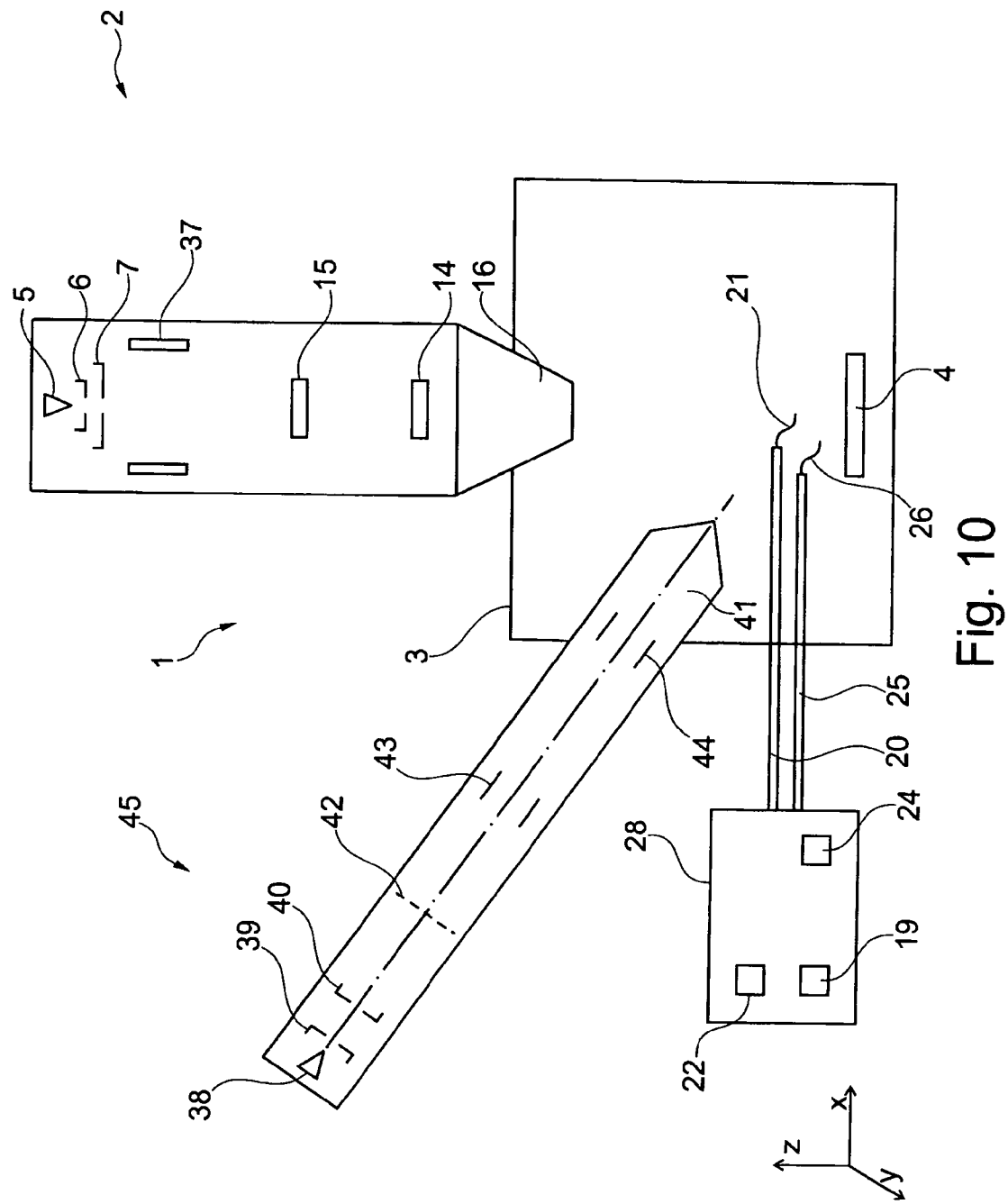
FIG. 10 shows a schematic view of another particle beam device having two particle beam columns and two movably positioned gas supply units.

FIG. 10 shows another particle beam device 1 having two particle beam columns, namely a first particle beam column 2 and a second particle beam column 45, and having a sample chamber 3. Particle beam device 1 of FIG. 10 may correspond to particle beam device 1 of FIG. 9. The same reference numerals therefore denote the same components. In contrast with particle beam device 1 according to FIG. 9, particle beam device 1 according to FIG. 10 has a gas inlet system 28, which is provided with a first gas tank system 19 and with a second gas tank system 24. Gas inlet system 28 of FIG. 10 corresponds to gas inlet system 28 of FIG. 2, so that reference is made to the preceding discussion for additional details.

Figure 11:
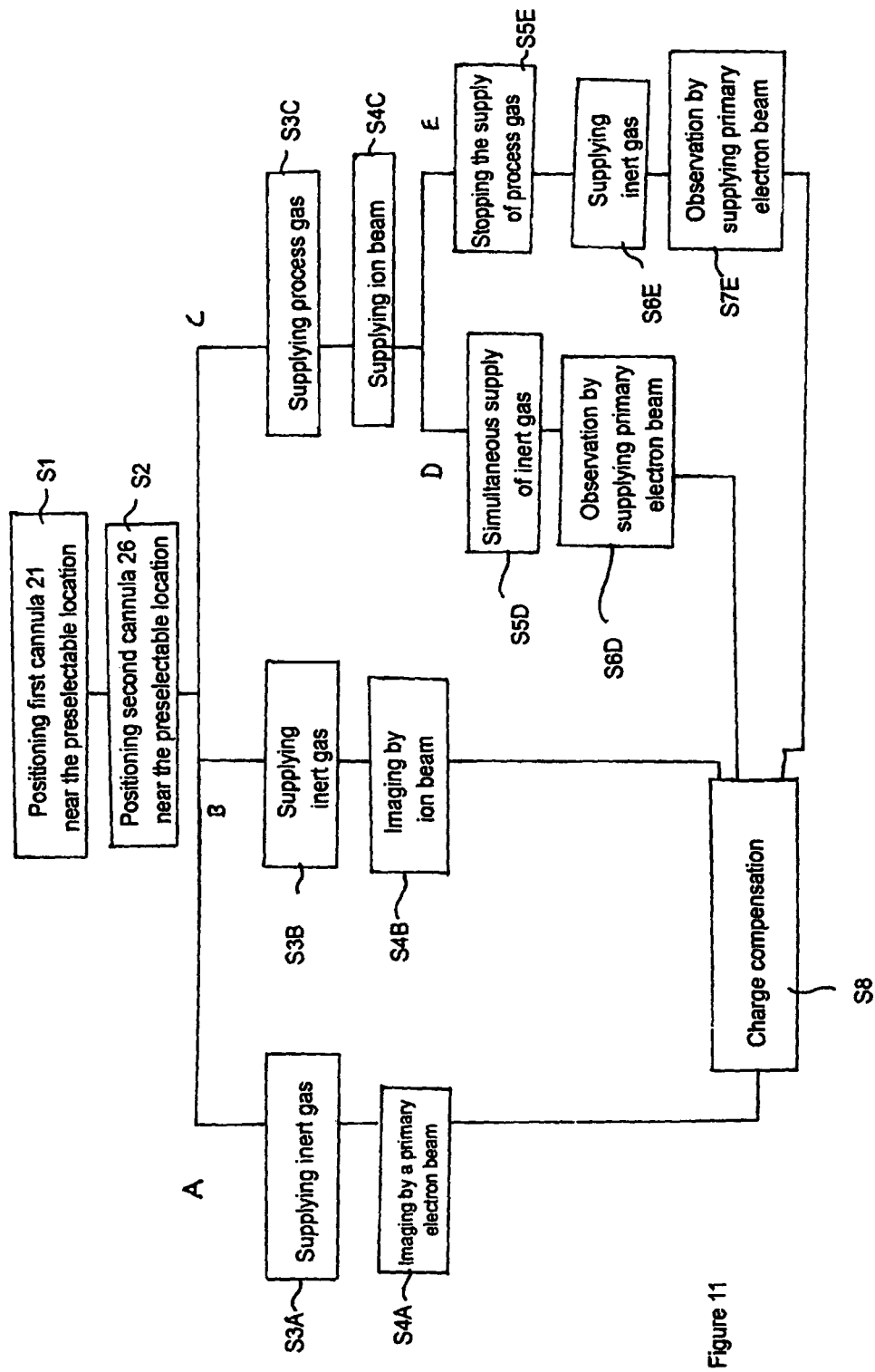
FIG. 11 shows a flow chart of a method which is used with the particle beam devices according to FIGS. 9 and 10.

FIG. 11 shows a flow chart of a method, which is used in connection with particle beam devices 1 according to FIGS. 9 and 10. In a step S1, first cannula 21 is brought into the vicinity of the preselectable location to be treated. In another step S2, second cannula 26 is brought into the vicinity of the preselectable location. It is possible to choose subsequently between three variants. In variant A, an ion beam is not directed at the surface of object 4, but instead the surface of object 4 is imaged by the primary electron beam of first particle beam column 2 (step S4A). Previously in step S3A, the inert gas has been supplied through first cannula 21.

In variant B, a primary electron beam is not directed at the surface of object 4 but instead the surface of object 4 is imaged by the ion beam of second particle beam column 45 (step S4B). Previously, in step S3B, the inert gas is supplied via first cannula 21.

In step S3C of variant C, the process gas is guided to the preselectable location via second cannula 26. For example, the partial pressure of the process gas is in the range of 0.01 Pa to 0.5 Pa or in the range of 0.05 Pa to 0.3 Pa, for example. In step S4C, the ion beam is brought to the preselectable location to induce a treatment operation by interaction with the process gas, e.g., removal of material or application of material. Subsequently, a choice may be made between two subvariants. In step S5D of subvariant D, the inert gas is supplied through first cannula 21 at the same time, whereupon the treatment operation is observed by first particle beam column 2 by imaging based on the primary electron beam at the same time (step S6D). In contrast, in step S5E of subvariant E, the supply of process gas is first stopped and only then in a step S6E is the inert gas supplied, in this step, observation occurring by imaging with the aid of first particle beam column 2 (step S7E). In both subvariants, the partial pressure of the inert gas is in the range of 20 Pa to 100 Pa or in the range of 30 Pa to 80 Pa, for example, or in the range of 40 Pa to 60 Pa, for example. The partial pressure of the process gas is much lower than the partial pressure of the inert gas. Again in this embodiment, a total pressure of less than or equal to 1 Pa prevails in sample chamber 3 during the entire method described here. Reference is again made to the above comments with regard to the partial pressures of the inert gas and the process gas and also with regard to the total pressure.

Method step S8 which follows is again the same for all variants. In this step, charge compensation takes place as already described above.

Figure 12:
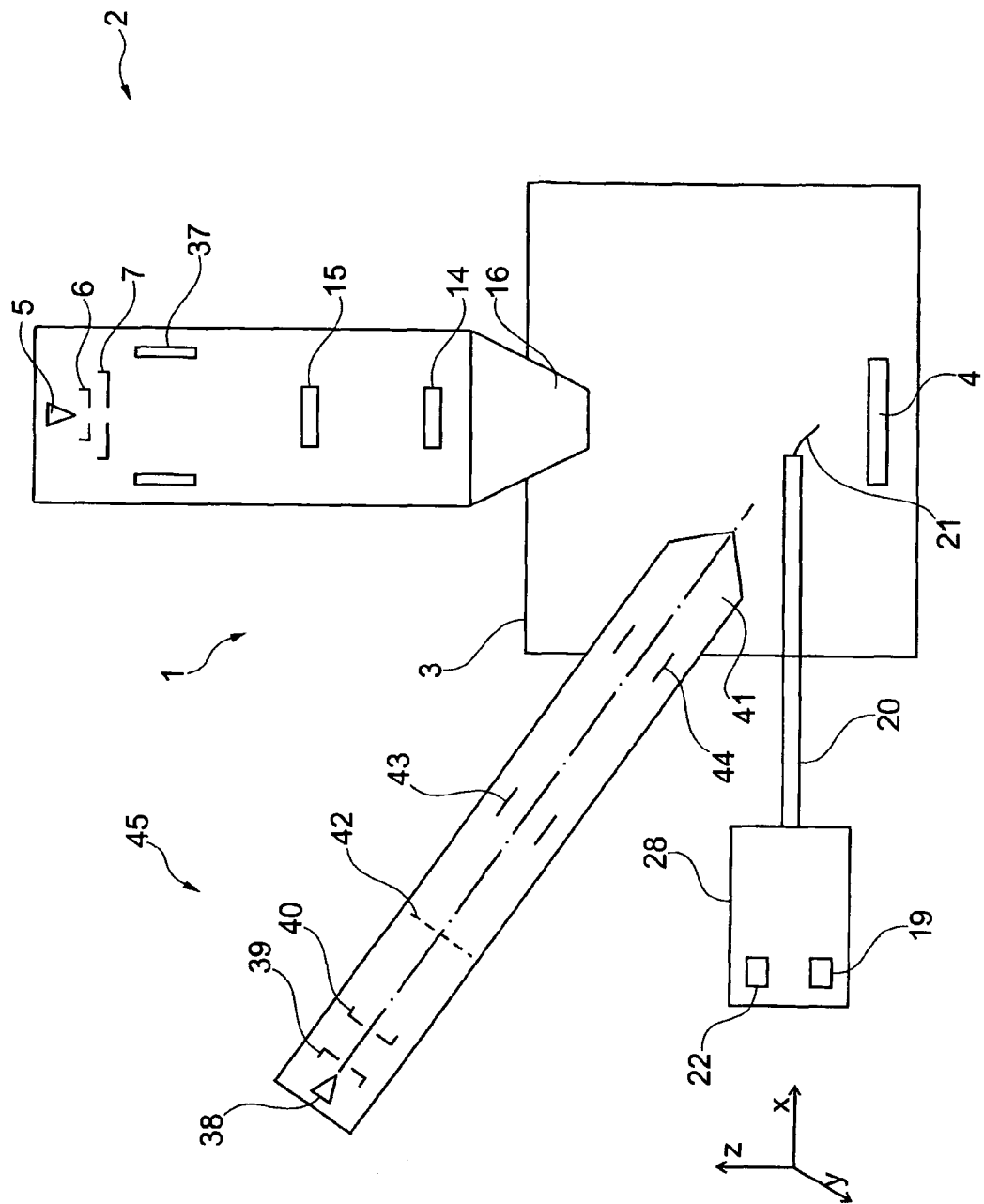
FIG. 12 shows a schematic view of another particle beam device having two particle beam columns and a single gas inlet system.

FIG. 12 shows another particle beam device 1 having a first particle beam column 2 and a second particle beam column 45 and having a sample chamber 3. Particle beam device 1 of FIG. 12 may correspond to particle beam device 1 of FIG. 9. The same reference numerals therefore denote the same components. In contrast with particle beam device 1 according to FIG. 9, particle beam device 1 according to FIG. 12 has a gas inlet system 28, which is provided with a gas tank system 19. Gas tank system 19 includes four process gases and two inert gases, which may be supplied individually to the preselectable location by triggering a valve system again through a first inlet line 20 and a first cannula 21. Gas inlet system 28 according to FIG. 12 may correspond to gas inlet system 28 according to FIG. 4, so that reference is made again to the preceding discussion for further details.

Figure 13:
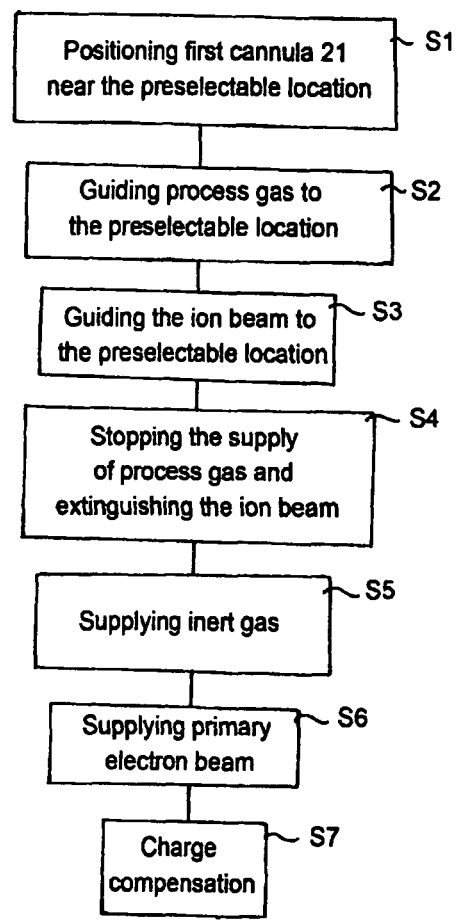
FIG. 13 shows a flow chart of a method used with the particle beam device according to FIG. 12.

The method used with particle beam device 1 according to FIG. 12 is shown schematically in FIG. 13. Thus, in a step S1, first cannula 21 is brought into the vicinity of the preselectable location. In step S2, the process gas is guided to the preselectable location via first cannula 21. For example, the partial pressure of the process gas is in the range of 0.01 Pa to 0.5 Pa or in the range of 0.05 Pa to 0.3 Pa, for example. In addition, in step S3, the ion beam is brought to the preselectable location to induce a treatment operation, e.g., removal of material or deposition of material, by interaction with the process gas. Next the supply of process gas is stopped and the ion beam is extinguished, so it is no longer focused on object 4 (step S4). In a step S5, the inert gas is then guided to the preselectable location. Next the primary electron beam is supplied, and in this step observation occurs via imaging by first particle beam column 2 (step S6). The partial pressure of the inert gas is in the range of 20 Pa to 100 Pa or in the range of 30 Pa to 80 Pa, for example, or in the range of 40 Pa to 60 Pa, for example. The partial pressure of the process gas is much lower than the partial pressure of the inert gas. In step S7, charge compensation again takes place. During the entire process, a total pressure of less than or equal to 1 Pa prevails in sample chamber 3. With regard to the partial pressures of the inert gas and the process gas, as well as the total pressure, reference is made to the preceding comments, which are also applicable here.

As explained above, the surface of object 4 to be examined may be contaminated with carbon, so that proper imaging of the surface of object 4 is very difficult. For this reason, in all the embodiments discussed above, a reactive gas or a mixture of a reactive gas with an inert gas may be supplied to the preselected location on the surface of object 4. Carbon may be removed from the preselected location on the surface of object 4 in this way. Room air or a mixture of nitrogen and oxygen is suitable as the reactive gas. In the particle beam devices described previously, gas supply units, in particular the gas supply units mentioned above, may be provided for supplying a reactive gas and/or a mixture of a reactive gas and an inert gas to the preselectable location on the surface of object 4.

Figure 14:
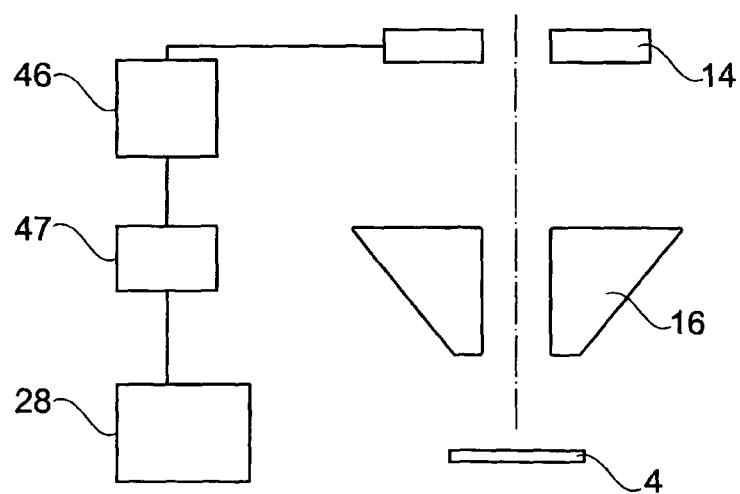
FIG. 14 shows a simplified view of a particle beam device having a control unit.

FIG. 14 shows a simplified view of a particle beam device based on particle beam device 1 according to FIG. 2. This shows detector 14, objective lens 16, and object 4. Furthermore, gas inlet system 28 is also shown. A control unit 47 is connected to gas inlet system 28 and to a high-voltage power supply unit 46 for applying a high voltage between detector 14 and object 4. Electrons emerging from object 4 and/or scattered on object 4 are accelerated in the direction of detector 14. Control unit 47 controls the flow of inert gas and process gas. It is designed so that the high voltage remains activated when the inert gas and/or the process gas is/are supplied.

Figure 15:
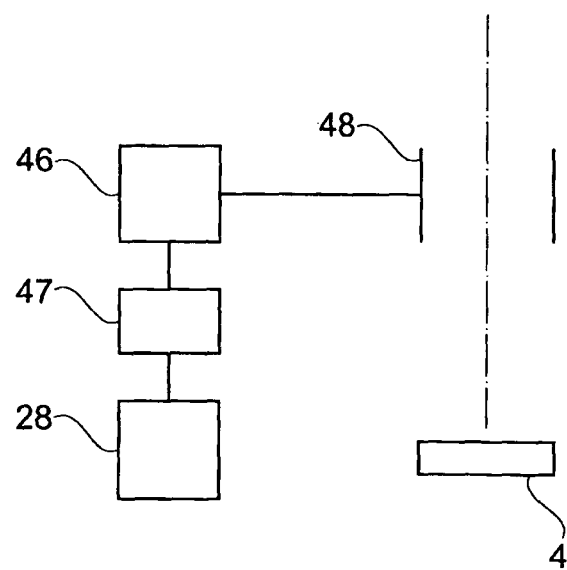
FIG. 15 shows another simplified view of a particle beam device having a control unit.

FIG. 15 shows a simplified view of another particle beam device based on particle beam device 1 according to FIG. 2. It shows an electrostatic lens 48 having two electrodes and object 4. Furthermore, gas inlet system 28 is also shown. A control unit 47 is connected to gas inlet system 28 and to a high-voltage power supply unit 46 for applying a high voltage between the electrodes of electrostatic lens 48. Control unit 47 controls the flow of inert gas and process gas and provides that the high voltage remains activated when the inert gas and/or the process gas is/are being supplied.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method for examining a surface of an object using a particle beam, the object being situated in a sample chamber, the method comprising:
   supplying the particle beam to a preselectable location on the surface of the object; and
   supplying at least one gas to the preselectable location, the gas being used for at least one of: charge neutralization at the preselectable location on the surface of the object, charge distribution away from the preselectable location on the surface of the object, and removal or avoidance of contamination of the object, wherein the gas has a partial pressure greater than or equal to 20 Pa, and wherein a total pressure in the sample chamber is less than or equal to 1 Pa during the supplying of the gas, wherein the gas is supplied as a first gas to the preselectable location on the surface of the object, and wherein a second gas is supplied to the preselectable location on the surface of the object, the second gas being used for treating the surface of the object at the preselectable location, wherein the partial pressure of the first gas is preselected as a first partial pressure, wherein the second gas has a second partial pressure, and wherein the first partial pressure is higher than the second partial pressure.

2. The method as recited in claim 1, wherein the gas supplied to the preselectable location is used for charge neutralization at the preselectable location on the surface of the object, for charge distribution away from the preselectable location on the surface of the object, and for removal or avoidance of contamination of the object.

3. The method as recited in claim 1, wherein the total pressure in the sample chamber during the supplying of gas is less than or equal to 0.5 Pa.

4. The method as recited in claim 3, wherein the total pressure during the supplying of the gas is less than or equal to 0.1 Pa.

5. The method as recited in claim 1, wherein the supply of the first gas and the supply of the second gas occur simultaneously.

6. The method as recited in claim 1, wherein the first gas is supplied only after the supply of the second gas is concluded.

7. The method as recited in claim 1, wherein the first partial pressure is in the range from 20 Pa to 100 Pa.

8. The method as recited in claim 7, wherein the first partial pressure is in the range from 30 Pa to 80 Pa.

9. The method as recited in claim 8, wherein the first partial pressure is in the range from 40 Pa to 60 Pa.

10. The method as recited in claim 1, wherein the second partial pressure is in the range from 0.01 Pa to 0.5 Pa.

11. The method as recited in claim 10, wherein the second partial pressure is in the range from 0.05 Pa to 0.3 Pa.

12. The method as recited in claim 1, wherein an inert gas is supplied as the first gas, and a process gas is supplied as the second gas.

13. The method as recited in claim 1, further comprising:
    guiding the particle beam to the surface as a first particle beam for generating an image of the surface of the object, wherein a second particle beam for treating the surface of the object is selected.

14. The method as recited in claim 1, further comprising:
    applying a high voltage potential between the object and a detector so that at least one of: particles emerging from the object and particles scattered on the object, are accelerated in the direction of the detector, the high voltage potential remaining activated during the supplying of the gas.

15. The method as recited in claim 1, further comprising:
    applying a high voltage potential between the object and an electrode of an electrostatic lens, the high voltage potential remaining activated during the supplying of the gas.

16. The method as recited in claim 1, further comprising:
    applying a high voltage potential between two electrodes of an electrostatic lens, the high voltage potential remaining activated during the supplying of the gas.

17. The method according to claim 1, further comprising:
    arranging at least one detector in at least one particle beam column that generates the particle beam, wherein the arranging the at least one detector includes arranging a first detector and a second detector in the at least one particle beam column.

18. The method according to claim 17, wherein the first detector and the second detector are offset from each other.

19. The method as recited in claim 1, further comprising:
    guiding the particle beam to the surface as a first particle beam for generating an image of the surface of the object, wherein a second particle beam for treating the surface of the object is selected.

20. A particle beam device, comprising:
    at least one particle beam column having at least one beam generator for generating a particle beam and at least one beam guidance system for guiding the particle beam;
    at least one sample chamber, wherein at least one object is positioned in the sample chamber, the object having a surface on which a preselectable location is located to which the particle beam is guidable by the beam guidance system; and at least one gas supply unit for supplying a gas to the preselectable location, the gas being used for at least one of: charge neutralization at the preselectable location on the surface of the object, charge distribution away from the preselectable location on the surface of the object, and removal or avoidance of contamination of the object, wherein the gas has a partial pressure greater than or equal to 20 Pa, and wherein a total pressure in the sample chamber is less than or equal to 1 Pa while the gas is being supplied, wherein the gas supply unit is a first gas supply unit for supplying a first gas to the preselectable location on the surface of the object, and wherein a second gas supply unit is provided for supplying a second gas to the preselectable location on the surface of the object, the second gas being provided for treating the surface of the object at the preselectable location, wherein the partial pressure of the first gas is preselected as a first partial pressure, wherein the second gas has a second partial pressure, and wherein the first partial pressure is higher than the second partial pressure.

21. The particle beam device according to claim 20, wherein the gas supplied by the at least one gas supply unit is used for charge neutralization at the preselectable location on the surface of the object, for charge distribution away from the preselectable location on the surface of the object, and for removal or avoidance of contamination of the object.

22. The particle beam device according to claim 20, wherein the total pressure in the sample chamber while the gas is being supplied is less than or equal to 0.5 Pa.

23. The particle beam device as recited in claim 22, wherein the total pressure is less than or equal to 0.1 Pa.

24. The particle beam device as recited in claim 20, wherein the first gas supply unit and the second gas supply unit operate independently of each other.

25. The particle beam device as recited in claim 20, wherein the first gas supply unit and the second gas supply unit are assigned to a single gas inlet system.

26. The particle beam device as recited in claim 20, wherein at least one of: the first gas supply unit and the second gas supply unit, are movable.

27. The particle beam device as recited in claim 20, wherein at least one of: the first gas supply unit and the second gas supply unit, have at least one cannula.

28. The particle beam device as recited in claim 27, wherein the cannula is movable.

29. The particle beam device as recited in claim 27, wherein the cannula has an inlet opening having a diameter in the range of 10 µm to 1000 µm.

30. The particle beam device as recited in claim 29, wherein the diameter of the inlet opening is in the range of 400 µm to 600 µm.

31. The particle beam device as recited in claim 20, wherein the first partial pressure is in the range of 20 Pa to 100 Pa.

32. The particle beam device as recited in claim 31, wherein the first partial pressure is in the range of 30 Pa to 80 Pa.

33. The particle beam device as recited in claim 32, wherein the first partial pressure is in the range of 40 Pa to 60 Pa.

34. The particle beam device as recited in claim 20, wherein the second partial pressure is in the range of 0.01 Pa to 0.5 Pa.

35. The particle beam device as recited in claim 34, wherein the second partial pressure is in the range of 0.05 Pa to 0.3 Pa.

36. The particle beam device as recited in claim 20, wherein the first gas is an inert gas, and wherein the second gas is a process gas.

37. The particle beam device as recited in claim 20, wherein the particle beam column is one of: an electron beam column and an ion beam column.

38. The particle beam device as recited in claim 20, further comprising:
at least one detector;
at least one high-voltage power supply unit that applies a high voltage between the detector and the object; and
at least one control unit which controls the flow of gas and the high-voltage power supply unit, wherein the control unit controls the high voltage to remain activated in at least one operating mode when the gas is supplied.

39. The particle beam device as recited in claim 38, wherein the at least one detector is arranged in the particle beam column and includes a first detector and a second detector.

40. The particle beam device as recited in claim 39, wherein the first detector and the second detector are offset from each other.

41. The particle beam device as recited in claim 20, further comprising:
an electrostatic lens having at least two electrodes;
at least one high-voltage power supply unit that applies a high voltage between the two electrodes of the electrostatic lens; and
at least one control unit that controls the flow of gas and the high-voltage power supply unit, wherein the control unit controls the high voltage to remain activated when the gas is supplied in at least one operating mode.

42. The particle beam device according to claim 20, wherein the particle beam column is a first particle beam column, the beam generator being provided as a first beam generator, which generates the particle beam in the form of a first particle beam, and the beam guidance system being provided as a first beam guidance system, and wherein a second particle beam column is also provided having a second beam generator for generating a second particle beam and having a second beam guidance system which guides the second particle beam to the preselectable location.

43. The particle beam device of claim 42, wherein the first particle beam column is an electron beam column, and wherein the second particle beam column is an ion beam column.

44. A method for examining a surface of an object using a particle beam, the object being situated in a sample chamber, the method comprising:
supplying the particle beam to a preselectable location on the surface of the object; and
supplying at least one gas to the preselectable location, wherein the gas has a partial pressure greater than or equal to 20 Pa, and wherein a total pressure in the sample chamber is less than or equal to 1 Pa during the supplying of the gas, wherein the gas is supplied as a first gas to the preselectable location on the surface of the object, and wherein a second gas is supplied to the preselectable location on the surface of the object, wherein the partial pressure of the first gas is preselected as a first partial pressure, wherein the second gas has a second partial pressure, and wherein the first partial pressure is higher than the second partial pressure.

45. The method according to claim 44, further comprising:
arranging at least one detector in at least one particle beam column that generates the particle beam.

46. The method according to claim 45, wherein arranging the at least one detector includes arranging a first detector and a second detector in the at least one particle beam column, wherein the first detector and the second detector are offset from each other.

47. The method as recited in claim 45, further comprising:
applying a high voltage potential between the object and the at least one detector so that at least one of: particles emerging from the object and particles scattered on the object, are accelerated in the direction of the at least one detector, the high voltage potential remaining activated during the supplying of the gas.

48. The method as recited in claim 44, wherein the supply of the first gas and the supply of the second gas occur simultaneously.

49. The method as recited in claim 44, wherein the first gas is supplied only after the supply of the second gas is concluded.

50. The method as recited in claim 44, wherein the first partial pressure is in the range from 20 Pa to 100 Pa.

51. The method as recited in claim 50, wherein the first partial pressure is in the range from 30 Pa to 80 Pa.

52. The method as recited in claim 51, wherein the first partial pressure is in the range from 40 Pa to 60 Pa.

53. The method as recited in claim 44, wherein the second partial pressure is in the range from 0.01 Pa to 0.5 Pa.

54. The method as recited in claim 53, wherein the second partial pressure is in the range from 0.05 Pa to 0.3 Pa.

55. The method as recited in claim 44, wherein an inert gas is supplied as the first gas, and a process gas is supplied as the second gas.

56. The method as recited in claim 44, further comprising:
guiding the particle beam to the surface as a first particle beam for generating an image of the surface of the object, wherein a second particle beam for treating the surface of the object is selected.

57. The method as recited in claim 44, further comprising:
applying a high voltage potential between the object and an electrode of an electrostatic lens, the high voltage potential remaining activated during the supplying of the gas.

58. The method as recited in claim 44, further comprising:
applying a high voltage potential between two electrodes of an electrostatic lens, the high voltage potential remaining activated during the supplying of the gas.

59. A particle beam device, comprising:
at least one particle beam column having at least one beam generator for generating a particle beam and at least one beam guidance system for guiding the particle beam;
at least one sample chamber, wherein at least one object is positioned in the sample chamber, the object having a surface on which a preselectable location is located to which the particle beam is guidable by the beam guidance system; and
at least one gas supply unit for supplying a gas to the preselectable location, wherein the gas has a partial pressure greater than or equal to 20 Pa, and wherein a total pressure in the sample chamber is less than or equal to 1 Pa while the gas is being supplied, wherein the gas supply unit is a first gas supply unit for supplying a first gas to the preselectable location on the surface of the object, and wherein a second gas supply unit is provided for supplying a second gas to the preselectable location on the surface of the object, wherein the partial pressure of the first gas is preselected as a first partial pressure, wherein the second gas has a second partial pressure, and wherein the first partial pressure is higher than the second partial pressure.

60. The particle beam device as recited in claim 59, further comprising:
at least one detector arranged in the particle beam column.

61. The particle beam device as recited in claim 60, wherein the at least one detector includes a first detector and a second detector, and wherein the first detector and the second detector are offset from each other.

62. The particle beam device as recited in claim 59, wherein the first partial pressure is in the range of 20 Pa to 100 Pa.

63. The particle beam device as recited in claim 62, wherein the first partial pressure is in the range of 30 Pa to 80 Pa.

64. The particle beam device as recited in claim 63, wherein the first partial pressure is in the range of 40 Pa to 60 Pa.

65. The particle beam device as recited in claim 59, wherein the second partial pressure is in the range of 0.01 Pa to 0.5 Pa.

66. The particle beam device as recited in claim 65, wherein the second partial pressure is in the range of 0.05 Pa to 0.3 Pa.

67. The particle beam device as recited in claim 59, wherein the first gas is an inert gas, and wherein the second gas is a process gas.

68. The particle beam device as recited in claim 59, wherein the particle beam column is one of: an electron beam column and an ion beam column.

69. The particle beam device as recited in claim 59, further comprising:
at least one detector;
at least one high-voltage power supply unit that applies a high voltage between the detector and the object; and
at least one control unit which controls the flow of gas and the high-voltage power supply unit, wherein the control unit controls the high voltage to remain activated in at least one operating mode when the gas is supplied.

70. The particle beam device as recited in claim 59, further comprising:
an electrostatic lens having at least two electrodes;
at least one high-voltage power supply unit that applies a high voltage between the two electrodes of the electrostatic lens; and
at least one control unit that controls the flow of gas and the high-voltage power supply unit, wherein the control unit controls the high voltage to remain activated when the gas is supplied in at least one operating mode.

71. The particle beam device as recited in claim 59, wherein the first gas supply unit and the second gas supply unit operate independently of each other.

72. The particle beam device as recited in claim 59, wherein the first gas supply unit and the second gas supply unit are assigned to a single gas inlet system.

* * * * *